(12) United States Patent
Ishiuchi (10) Patent No.: US 7,750,024 B2
(45) Date of Patent: Jul. 6, 2010

(54) REMEDY FOR GLIOBLASTOMA

(75) Inventor: Shogo Ishiuchi, Maebashi (JP)

(73) Assignee: Astellas Pharma Inc., Tokyo (JP)

( * ) Notice: Subject to any disclaimer, the term of this patent is extended or adjusted under 35 U.S.C. 154(b) by 1502 days.

(21) Appl. No.: 10/509,379

(22) PCT Filed: Mar. 27, 2003

(86) PCT No.: PCT/JP03/03867

§ 371 (c)(1),
(2), (4) Date: Sep. 27, 2004

(87) PCT Pub. No.: WO03/082332

PCT Pub. Date: Oct. 9, 2003

(65) Prior Publication Data

US 2005/0165009 A1    Jul. 28, 2005

(30) Foreign Application Priority Data

Mar. 29, 2002  (JP) ............................ 2002-094313

(51) Int. Cl.
*A61K 31/47* (2006.01)
(52) U.S. Cl. ..................................................... 514/310
(58) Field of Classification Search .................. 514/310
See application file for complete search history.

(56) References Cited

U.S. PATENT DOCUMENTS

| | | | |
|---|---|---|---|
| 5,639,751 A * | 6/1997 | Andrasi et al. ............... | 514/220 |
| 6,096,743 A | 8/2000 | Shishikura et al. | |
| 6,133,258 A | 10/2000 | Shishikura et al. | |

FOREIGN PATENT DOCUMENTS

| | | |
|---|---|---|
| WO | WO 96/10023 A1 | 4/1996 |
| WO | WO 97/17970 A1 | 5/1997 |
| WO | WO 00/24395 A1 | 5/2000 |
| WO | WO 00/54772 A1 | 9/2000 |
| WO | WO 03/000928 A2 | 1/2003 |
| WO | WO 2004/014433 A1 | 2/2004 |

OTHER PUBLICATIONS

Jeffrey D. Rothstein et al., "Excitotoxic destruction facilitates brain tumor growth", Nature Medicine (2001), vol. 7, No. 9, pp. 994-995.
Mark Noble, "Can neural stem cells be used as therapeutic vehicles in the treatment of brain tumors?", Nature Medicine, vol. 6, No. 4, pp. 369-370 (Apr. 2000).
Wojciech Rzeski, et al., "Glutamate antagonists limit tumor growth", Proceedings of the National Academy of Sciences of United States of America, vol. 98, No. 11, pp. 6372-6377 (May 22, 2001).
Shogo Ishiuchi, et al., "Blockage of $Ca^{2+}$-permeable AMPA receptors suppresses migration and induces apoptosis in human glioblastoma cells", Nature Medicine, vol. 8, No. 9, pp. 971-978, (Sep. 2002).
Catarina L. Florian, et al., "Characteristics Metabolic Profiles Revealed by $^1$H NMR Spectroscopy for Three Types of Human Brain and Nervous Systems Tumours", NMR in Biomedicine, vol. 8, pp. 253-264, (1996).
Takahiro Takano, et al., "Glutamate release promotes growth of malignant gliomas", Nature Medicine, vol. 7, No. 9, pp. 1010-1015 (2001).
International Search Report, JPO, Jun. 17, 2003.
Ishiuchi, S. et al., "A Crucial Role of $Ca^{2+}$-Permeable AMPA Receptors in Human Glioblastoma Cells", Jikken Igaku—Experimental Medicine, 2002, pp. 2651-2653, vol. 20, No. 18, XP 008070096.
Labrakakis, C. et al., "Glutamate Receptor Activation Can Trigger Electrical Activity in Human Glioma Cells", European Journal of Neuroscience, Jun. 1998, pp. 2153-2162, vol. 10, No. 6, XP 002558225.
Ishiuchi, S. et al., "Extension of Glial Processes by Activation of $Ca^{2+}$-Permeable AMPA Receptor Channels", Neuroreport, Mar. 2001, pp. 745-748, vol. 12, No. 4, XP 002974830.
Ye, Z.-C. et al., "Glioma Cells Release Excitotoxic Concentrations of Glutamate", Cancer Research, Sep. 1999, pp. 4383-4391, vol. 59, No. 17, American Association for Cancer Research, Baltimore, MD, XP 002331150.
Supplementary European Search Report issued in counterpart European Patent Application No. 03715539.7 dated Dec. 11, 2009.

* cited by examiner

*Primary Examiner*—Gollamudi S. Kishore
*Assistant Examiner*—Snigdha Maewall
(74) *Attorney, Agent, or Firm*—Sughrue Mion, PLLC

(57) ABSTRACT

It is an object of the present invention to provide a novel therapeutic agent for glioblastoma.

In accordance with the present invention, it was found that compounds having an antagonistic action against AMPA receptor are useful as therapeutic agents for glioblastoma, particularly primary glioblastoma de novo with a high malignancy level, and the object has been attained.

2 Claims, 1 Drawing Sheet

FIG. 1

REMEDY FOR GLIOBLASTOMA

This is a National Stage application under 35 U.S.C. §371 of PCT/JP03/03867 filed on Mar. 27, 2003 which claims priority from Japanese Patent Application 2002-094313 filed on Mar. 29, 2002, all of which are incorporated herein by reference.

TECHNICAL FIELD

The present invention relates to a novel pharmaceutical use of a compound having an antagonistic action against AMPA receptor as a therapeutic agent for glioblastoma.

BACKGROUND OF THE INVENTION

Glioma is the general name of tumors originating from ependymoblasts, which is the stem cell for glia, in the course of the differentiation thereof into ependymal cell, astroglia and oligodendroglia [Seikagaku Jiten (Dictionary of Biochemistry), the third edition, Tokyo Kagaku Dojin, Tokyo, 1998].

Glioblastoms multiforme (referred to as glioblastoma hereinafter) highly invades the central nervous system and is ranked at a higher malignancy level among gliomas. Thus, glioblastoma is a typical one of malignant brain tumors.

Additionally, the lethal rate thereof is very high so that the onset thereof induces death in 9 to 12 months. Even today with the progress in the various therapeutic methods thereof, the 5-year survival from 1986 to 1990 is 8.0%, compared with the 5-year survival 20 years ago namely the 5-year survival from 1969 to 1975, which was 11.9%. Thus, almost no difference is observed (Neurology Progress, 43(3), 338-350, 1999). Accordingly, it is strongly desired that an effective therapeutic method thereof should be established.

Tumor cells of glioblastoma are the most undifferentiated among brain tumors, so the tumor cells have high potentials of migration and proliferation and are highly invasive, leading to very poor prognosis.

Glioblastoma is classified into primary glioblastoma de novo and secondary glioblastoma, depending on the difference in the gene mechanism of the malignant transformation of undifferentiated astrocyte or precursor cells. Secondary glioblastoma occurs in a young generation of 45 years old or younger. In 4 to 5 years on average, secondary glioblastoma occurs from astrocytoma through undifferentiated astrocytoma. Meanwhile, primary glioblastoma de novo frequently occurs in an older generation of the mean age of 55 years old. Generally, primary glioblastoma de novo takes the form of fulminant glioblastoma (referred to as de novo glioblastoma as well) which occurs within 3 months from the state with no clinical or pathological abnormalities [Pathology and Genetics of the Nervous Systems. 29-39 (IARC Press, Lyon, France, 2000)].

Glioblastoma migrates along myelinated nerve and spreads widely in the central nerve. Therefore, surgical treatment thereof cannot show any satisfactory therapeutic effect (Neurol. Med. Chir. (Tokyo) 34, 91-94, 1994; Neurol. Med. Chir. (Tokyo) 33, 425-458, 1993; Neuropathology 17, 186-188, 1997). Additionally, pharmaceutical agents with an indication for glioblastoma are limited in Japan to for example ranimustine and interferon. Additionally, the efficacy thereof is insufficient.

α-amino-3-hydroxy-5-methyl-4-isoxazole propionic acid (AMPA)-type glutamate receptors belong to ionotropic glutamate receptors are responsible for rapid nerve conduction of almost all excitatory synapses (Trends Neurosci. 16, 359-365, 1993; Annu. Rev. Neurosci. 17, 31-108, 1994; Prog. Neurobiol. 54, 581-618, 1998). AMPA receptors are expressed in many glyacytes like those in neurons (Trends Pharmacol. Sci. 21, 252-258, 2000). AMPA receptors are composed of four subunits, namely GluR1 through GluR4. The $Ca^{2+}$ permeability of an AMPA receptor depends on the composition with the subunits thereof. Specifically, an AMPA receptor with the GluR2 subunit has low $Ca^{2+}$ permeability, while an AMPA receptor without GluR2 has high $Ca^{2+}$ permeability. A higher content of the GluR2 subunit decreases the $Ca^{2+}$ permeability more (Trends Neurosci. 16, 359-365, 1993; Annu. Rev. Neurosci. 17, 31-108, 1994; Prog. Neurobiol. 54, 581-618, 1998). Further, the unique feature of GluR2 is described as follows. In case that one amino acid residue in the second hydrophobic region (M2), which is originally arginine (R), is substituted with glutamine (Q), the resulting homomer receptor composed of the substituted GluR2(Q) has high $Ca^{2+}$ permeability (Trends Neurosci. 16, 359-365, 1993; Annu. Rev. Neurosci. 17, 31-108, 1994). In other words, such receptor at a higher content of the GluR2 subunit when the subunit is GluR(Q) type is highly permeable to $Ca^{2+}$. When the subunit is GluR2(R), however, the resulting receptor does not shows any $Ca^{2+}$ permeability.

Concerning glioma cells and glutamate, reports showed that the expression of the GluR2 gene is low in C6-glioma (J. Neurosci. Res. 46, 164-178, 1996) and that 66% of glioblastoma culture cells respond to a glutamate receptor agonist and depolarize (Eur. J. Neurosci. 10, 2153-2162, 1998).

The following reports have been issued about the inhibiting action of antagonists against the ionotropic glutamate receptor family on glioma and the like.

1) Patent reference 1 discloses an invention relating to the method for inhibiting the interaction between AMPA receptor complexes and glutamate for cancer treatment, wherein specific examples of brain tumor include medulloblastoma classified as a fetal tumor and human brain astrocytoma as one glioma type. The Reference describes the in vitro effect of an antagonist GYK152446 against AMPA receptor on brain astrocytoma.

However, the reference does not disclose or suggests the use of the antagonist against AMPA receptor for treatment of glioblastoma with high malignancy to have resistance to radiotherapy or chemotherapy.

2) Non-patent reference 1 by the inventor described above includes a description that antagonists against NMDA- and AMPA receptors are highly sensitive to tumor cells derived from peripheral cells but poorly sensitive to tumor cells derived from nerve and glyacites. Additionally, the reference describes that these antagonists are useful as therapeutic agents of peripheral cancer. Thus, the effect of the invention on glioblastoma cannot be anticipated on the basis of the in vitro effect using the tumor cells with lower malignancy levels than that of glioblastoma.

3) Non-patent reference 2 reports that MK-801 and memantin as antagonists against NMDA receptor exert a proliferation inhibition in the C6 and RG2 glioma transplanted rat models.

However, it is criticized that the previous research on glioma using such animal models are criticized since they do not represent real growth of tumor (non-patent Reference 3).

4) Additionally, non-patent reference 4 as one critical review of the non-patent reference 1 suggests the possibility of the inhibition AMPA receptors and NMDA receptors as a multiple therapy for glioma. However, the authors are suspicious about whether or not the animal models using C6 and RG2 glioma used in the non-patent reference 1 can reflect human tumor.

Based on those described above, these previous techniques do not include any specific descriptions about the possibility that antagonists against AMPA receptor will become a therapeutic agent of the most malignant human glioblastoma among various types of glioma. The effect on C6 and RG2 glioma does not suggest any possible therapeutic effect on human glioblastoma.

Thus, the invention is not described in any these previous techniques, and it cannot be derived readily from them.

[Patent Reference 1]
PCT International Publication pamphlet WO 00/24395

[Non-Patent Reference 1]
Proceedings of the National Academy of Sciences of United States of America 98 (11), 6372-6377, 2001

[Non-Patent Reference 2]
Nature Medicine 7(9), 1010-1015, 2001

[Non-Patent Reference 3]
Nature Medicine 6(4), 369-370, 2000

[Non-Patent Reference 4]
Nature Medicine 7(9), 994-995, 2001

Disclosure of the Invention

It is an objective of the invention to provide a therapeutic agent for glioblastoma, which has a novel action mechanism.

The inventors made investigations so as to attain the object. The inventors found that the GluR1 and/or GluR4 subunit was expressed widely in glioblastoma cells, particularly human primary glioblastoma cell and functioned as a $Ca^{2+}$-permeable AMPA receptor. Specifically, the inventors found that the transformation of biological $Ca^{2+}$-permeable AMPA receptor into $Ca^{2+}$-non-permeable AMPA receptor by transfection of the GluR2(R) gene with adenovirus vector inhibited migration and induced the apoptosis of glioblastoma cells. In other words, the inhibition of $Ca^{2+}$ permeability by the presence of the subunit GluR2(R) induces the cell death of glioblastoma cells. Further, the inventors found that in contrast, excess expression of $Ca^{2+}$-permeable AMPA receptor promoted not only the morphological change and growth of the tumor cell but also the migration ability.

Still further, the inventor established an animal model highly reflecting the pathological feature of human glioblastoma and used this model for verifying the effect in accordance with the invention. The animal model with a transplanted human glioblastoma cell line CGNH-89 as established by the inventor reflects the pathological feature of human glioblastoma, where the cell vigorously invades the inside of brain parenchyma and the subpial brain to induce meningeal dissemination.

Accordingly, the inventors certified that a compound, which has high antagonistic effect against AMPA receptor inhibits tumor growth in an animal model reflecting human glioblastoma, based on the findings that the AMPA receptors of glioblastoma cell were composed of the GluR1 and/or GluR4 subunit not GluR2 and the high $Ca^{2+}$ permeability of the AMPA receptor was responsible for the marked growth and migration abilities of human glioblastoma cell. Thus, the invention has been achieved.

Therefore, the present invention relates to a therapeutic agent for glioblastoma, which comprises a compound having an activity of inhibiting an AMPA receptor as the active ingredient.

Preferably, the present invention relates to a therapeutic agent for glioblastoma, wherein the compound having an activity of inhibiting an AMPA receptor is [7-(1H-imidazol-1-yl)-6-nitro-2,3-dioxo-3,4-dihydroquinoxalin-1(2H)-yl] acetic acid or a salt thereof or a hydrate thereof.

Additionally, the present invention relates to a therapeutic agent for glioblastoma, wherein the compound having an activity of inhibiting an AMPA receptor is 2,3-dihydroxy-6-nitro-7-sulfamoyl-benzo(F)-quinoxaline or a salt thereof.

Still additionally, the present invention relates to a therapeutic agent for glioblastoma, wherein the compound having an activity of inhibiting an AMPA receptor is 2-[N-(4-chlorophenyl)-N-methylamino]-4H-pyrido[3,2-e]-1,3-thiazin-4-one or a salt thereof.

Additionally, the present invention relates to a pharmaceutical composition for a therapeutic agent for glioblastoma, which comprises a therapeutically effective amount of a compound having an activity of inhibiting an AMPA receptor and a pharmaceutically acceptable carrier;

the aforementioned pharmaceutical composition wherein the compound having an activity of inhibiting an AMPA receptor is preferably [7-(1H-imidazol-1-yl)-6-nitro-2,3-dioxo-3,4-dihydroquinoxalin-1(2H)-yl]acetic acid or a salt thereof or a hydrate thereof;

the aforementioned pharmaceutical composition wherein the compound having an activity of inhibiting an AMPA receptor is preferably 2,3-dihydroxy-6-nitro-7-sulfamoyl-benzo(F)-quinoxaline or a salt thereof; and the aforementioned pharmaceutical composition wherein the compound having an activity of inhibiting an AMPA receptor is preferably 2-[N-(4-chlorophenyl)-N-methylamino]-4H-pyrido[3,2-e]-1,3-thiazin-4-one or a salt thereof.

Still more, the present invention relates to the use of a compound having an activity of inhibiting an AMPA receptor for the manufacture of a medicament for treating glioblastoma comprising a clinically effective amount of the compound;

the aforementioned use thereof wherein the compound having an activity of inhibiting an AMPA receptor is preferably [7-(1H-imidazol-1-yl)-6-nitro-2,3-dioxo-3,4-dihydroquinoxalin-1(2H)-yl]acetic acid or a salt thereof or a hydrate thereof;

the aforementioned use thereof wherein the compound having an activity of inhibiting an AMPA receptor is preferably 2,3-dihydroxy-6-nitro-7-sulfamoyl-benzo(F)-quinoxaline or a salt thereof; and the aforementioned use thereof wherein the compound having an activity of inhibiting an AMPA receptor is preferably 2-[N-(4-chlorophenyl)-N-methylamino]-4H-pyrido[3,2-e]-1,3-thiazin-4-one or a salt thereof or a hydrate thereof.

Furthermore, the present invention relates to a method for treating glioblastoma comprising administering a therapeutically effective amount of a compound having an activity of inhibiting an AMPA receptor to a patient with the disease; such method wherein the compound having an activity of inhibiting an AMPA receptor is preferably [7-(1H-imidazol-1-yl)-6-nitro-2,3-dioxo-3,4-dihydroquinoxalin-1(2H)-yl] acetic acid or a salt thereof or a hydrate thereof;

the aforementioned method wherein the compound having an activity of inhibiting an AMPA receptor is preferably 2,3-dihydroxy-6-nitro-7-sulfamoyl-benzo(F)-quinoxaline or a salt thereof; and the aforementioned method wherein the compound having an activity of inhibiting an AMPA receptor is preferably 2-[N-(4-chlorophenyl)-N-methylamino]-4H-pyrido[3,2-e]-1,3-thiazin-4-one or a salt thereof.

BEST MODE FOR CARRYING OUT THE INVENTION

The present invention is now described in details as follows.

Glioblastoma means primary glioblastoma de novo and secondary glioblastoma, preferably primary glioblastoma de novo.

The therapeutic agent for glioblastoma means having an effect of inhibiting growth of glioblastoma, an effect of prolonging the survival period, or an effect of raising the survival rate.

The effect of inhibiting growth of glioblastoma means an effect of reducing or not increasing the volume of glioblastoma when the compound for use in accordance with the present invention is administered to an animal, preferably a human patient with the onset of glioblastoma, compared with the volume thereof when no such compound is administered.

The effect of prolonging the survival period means an effect of prolonging the survival period when the compound for use in accordance with the present invention is administered to an animal, preferably a human patient with the onset of glioblastoma, compared with the mean survival period when none of various therapeutic treatments indicated for the disease or no treatment is done. Preferably, the effect means an effect of significantly prolonging the survival period.

The effect of raising the survival rate means an effect of raising the survival rate during a period of one month to 12 months, a period of one year to 5 years or a period of 5 years or longer when the compound for use in accordance with the present invention is administered to an animal, preferably a human patient with the onset of glioblastoma, compared with the survival rate when none of various therapeutic treatments indicated for the disease or no treatment is done. Preferably, the effect means an effect of significantly raising the survival rate.

The compound usable in accordance with the present invention is a compound inhibiting the AMPA-type glutamate receptor.

The compound with an activity inhibiting the AMPA receptor includes a compound binding to the ligand binding site of the AMPA receptor in a competitive or non-competitive manner to inhibit the binding between the AMPA receptor and glutamate; or a compound not binding to the binding site of the AMPA receptor but binding to the allosteric regulation site of the AMPA receptor, thus, block the glutamate neurotransmission.

Preferably, the compound is 2,3-dihydroxy-6-nitro-7-sulfamoyl-benzo(F)-quinoxaline (NBQX), [7-(1H-imidazol-1-yl)-6-nitro-2,3-dioxo-3,4-dihydroquinoxalin-1(2H)-yl]acetic acid (zonanpanel) disclosed as an antagonist against AMPA receptor in WO 96/10023, or a salt thereof, or 2-[N-(4-chlorophenyl)-N-methylamino]-4H-pyrido[3,2-e]-1,3-thiazin-4-one (referred to as compound B hereinbelow) or a salt thereof.

[7-(1H-Imidazol-1-yl)-6-nitro-2,3-dioxo-3,4-dihydroquinoxalin-1(2H)-yl]acetic acid forms a salt with an acid or a base. Preferably, the salt is a pharmaceutically acceptable salt.

The salt with an acid includes acid addition salts with inorganic acids such as mineral acids including hydrochloric acid, hydrobromic acid, hydroiodic acid, sulfuric acid, nitric acid, and phosphoric acid, and organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, and glutamate. The salt with a base includes for example salts with inorganic bases such as sodium, potassium, magnesium, calcium and aluminium, organic bases such as methylamine, ethylamine, and ethanolamine, or salts with basic amino acids such as arginine and ornithine, and ammonium salt. Furthermore, the compound may form hydrates, solvates with ethanol and the like, crystal polymorphism.

Preferably, the compound is [7-(1H-imidazol-1-yl)-6-nitro-2,3-dioxo-3,4-dihydroquinoxalin-1 (2H)-yl]acetic acid•monohydrate (compound A).

2-[N-(4-Chlorophenyl)-N-methylamino]-4H-pyrido[3,2-e]-1,3-thiazin-4-one (compound B) may form a salt with an acid. The salt with an acid includes for example inorganic acids such as hydrochloric acid, hydrobromic acid, hydroiodic acid, sulfuric acid, nitric acid, and phosphoric acid, and organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, and acidic amino acids such as aspartate and glutamate. Preferably, the compound is in the free form.

Furthermore, compound B or a salt thereof may sometimes be isolated in the form of various solvates such as hydrate and ethanol solvate or in the form of substances in polymorphic crystal thereof. The compound B encompasses such various hydrates, solvates and substances in polymorphic crystal thereof.

Other than the compounds described above, antagonists against AMPA receptor include those described below in the table.

| Compound name | Original supplier company | References, etc. |
|---|---|---|
| CX 516 1-(Piperidin-1-yl-)-1-(quinoxalin-6-yl)methanone | Cortex Pharmaceuticals' | International Clinical Psychopharmacology. 11: 13– Mar. 19, 1996. |
| LU-73068 4,5-Dihydro-1-methyl-4-oxo-7-(trifluoromethyl)-imidazo[1,2-a]quinoxaline-2-carboxylic acid | Abbott GmbH & Co. KG | British Journal of Pharmacology. 125: 1258–1266, Nov 1998. Germany |

| Compound name | Original supplier company | References, etc. |
|---|---|---|
| LU 115455<br>N-((1-(1-Carboxymethyl-5,6,7,8-tetrahydro-benzo [f] quinoxaline-2,3-(1H,4H)-dion-9-yl)-pyrrol-3-yl)methyl-N'-(4-carboxyphenyl)-urea | Abbott GmbH & Co. KG | European Journal of Neuroscience. 11: 250–262, Jan. 1999. |
| Aloracetam | Aventis | RN119610-26-3 |
|  | Aventis | WO 9512594 |
| Irampanel | Boehringer Ingelheim | RN206260-33-5<br>WO 9817652 |
| E-2007<br>Amino-3-hydroxy-5-methyl-4-isoxazolepropionate | Eisai Co., Ltd. | Pharmaprojects No. 6432 |
| LY 215490<br>6-[2-(1H-Tetrazol-5-yl)ethyl]decahydroisoquinoline-3-carboxylic acid | Eli Lilly | Journal of Medicinal Chemistry. 36: 2046–2048, Jul. 9, 1993 |
| LY-293558<br>(3S,4aR,6R,8aR)-Decahydro-6-[2-(1H-tetrazol-5-yl)ethyl]-3-Isoquinolinecarboxylic acid | Eli Lilly | Journal of Medicinal Chemistry. 36: 2046–2048, Jul. 9, 1993 |
| LY-311446<br>2-Amino-3-[2-[3-(1H-tetrazol-5-yl)phenoxy]phenyl]propionic acid | Eli Lilly | Pharmaprojects Accession No.: 24859 |
| LY 326325<br>(−)(3S,4aR,6R,8aR)-6-[2-(1(2) H-Tetrazole-5-yl)ethyl] 1,2,3,4,4a,5,6,7,8,8a-decahydroisoquinoline-3-carboxylic acid monohydrate | Eli Lilly | Biochemical Pharmacology. 50: 1761–1774, Nov. 27, 1995 |
| LY-377770 | Eli Lilly | Neuropharmacology, (2000), 39(9), 1575–1588 |
|  | | |
| LY-404187 | Eli Lilly | Neuropharmacology, (2001), 40(8), 1003–1009 |
|  | | |
| 3-Methylsulfonylamino-6,7-dinitro-2(1H)-quinoxalinone | FujisawaPharmaceutical Co., Ltd. | WO 9732858 |
| GYKI-47261<br>6-(Aminophenyl)-8-chloro-2-methyl-11H-imidazo[1,2-c][2,3]benzodiazepine | IVAX | WO 9906408 |
| GYKI 52466<br>1-(4-Aminophenyl)-4-methyl-7,8-methylenedioxy-5H-2,3-benzodiazepine | IVAX Drug Research Institute | Journal of Neural Transmission-Parkinson's Disease and Dementia Section. 9: 145–149, No. 2–3, 1995 |
| GYKI-53655<br>5-(4-Aminophenyl)-8,9-dihydro-N,8-dimethyl-7H-1,3-Dioxolo[4,5-h][2,3]benzodiazepine-7-carboxamide monohydrochloride | IVAX | European Journal of Pharmacology. 331: 93–96, 16 Jul. 1997 |

| Compound name | Original supplier company | References, etc. |
|---|---|---|
| GYKI 152466 | Solvay | Society for Neuroscience Abstracts. 26: 2100, Part 2, 2000. |
| Talampanel | IVAX | RN161832-65-1 U.S. Pat. No. 5639751 |
| RWJ 37947 2,3-O-Isopropylidene-4,5-O-sulfonyl-β-D-fructopyranonse 1-O-sulfamate | Johnson & Johnson Pharmaceutical Res. & Development LLC | Bioorganic and Medicinal Chemistry Letters. 3: 2653–2656, Dec. 1993. USA |
| KRP-199 6-Trifluoromethyl-3-oxo-7-[4-(4-carboxyphenylaminocarbonyloxymethyl)imi-dazol-1]1-3,4-Dihydroquinoxaline-2-carboxylic acid | Kyorin Pharmaceutical Co., Ltd. | Abstracts of Papers, 223rd ACS National Meeting, Orlando, FL, United States, Apr. 7–11, 2002 (2002), MEDI-042 Publisher: American Chemical Society |
| NS-1029 2-[[[5-[4-[(Dimethylamino)sulfonyl]phenyl]-1,2,6,7,8,9-hexahydro-8-methyl-2-oxo-3H-pyrrolo[3,2-h]isoquinolin-3-ylidene]amino]oxy]-3-hydroxy-Butanoic acid | NeuroSearch | RN254751-28-5 WO 9426747 |
| NS 229 3-(Hydroxyimino)-N,N-dimethyl-2-oxo-2,3,6,7,8,9-hexahydro-1H-benzo [g] indole-5-sulfonamide | NeuroSearch | ADIS R&D Insight Accession Number: 15670 |
| PNQX 9-Methyl-6-nitro-1,4,7,8,9,10-hexahydropyrido [3,4-f] quinoxaline-2,3-dione | NeuroSearch | Stroke. 30: 1472–1477, Jul. 1999. USA |
| COMP | Neurotech Pharm | Pharmaprojects Accession No.: 32452 |
| AMP-397 7-Nitro-5-(phosphonomethylamino)methyl 1,3-Dihydro-quinoxalin-2,3-dione | Novartis | American Chemical Society National Meeting.: abstr. MEDI 14, Mar. 26, 2000. Switzerland |
| NNC-07-0775 | Novo Nordisk | WO 9615100 |
| NNC-07-9202 2-Carboxy-1-methyl-7-trifluoromethylimidazo[1,2-a]quinoxalin-4(5H)-one | Novo Nordisk | EP 283959 WO 9521842 |
| NBQX | Novo Nordisk | Journal of the Neurological Sciences. 119: 209–216, Nov 1993 |
| L 698544 (CNDQ) 7-Chloro-3-nitro-1,2,3,4-tetrahydroquinolin-2-one | Merck & Co | ADIS R&D Insight Accession Number: 3218 |
| PD-159265 N-Methyl-N-(6-methyl-7-nitro-2,3-dioxo-1,2,3,4-tetrahydroquinoxalin-5-ylmethyl)glycine | Pfizer Global Res. & Development | 215th American Chemical Society National Meeting. 215: abstr. MEDI 014, Mar. 29, 1998. USA |
| PD 160725 | Pfizer Global Res. & Development | 215th American Chemical Society National Meeting. 215: abstr. MEDI 014, Mar. 29, 1998. USA |
| CP-465022-27 6-Fluoro-3-(2-chlorophenyl)-2-[(6-diethylaminomethyl)pyridin-2-yl] ethenyl-Quinazolin-4-one | Pfizer | Society for Neuroscience Abstracts. 24: 99, Part 1, 1998. USA |
| NS-257 1,2,3,6,7,8-Hexahydro-3-(hydroxyimino)-N,N,7-trimethyl-2-oxo-Benzo[2,1-b:3,4-c']dipyrrole-5-sulfonamide | NeuroSearch | RN147750-87-6 |
| PNQX | Pfizer | Journal of Medicinal Chemistry (1999), 42(12), 2266–2271 |

-continued

| Compound name | Original supplier company | References, etc. |
|---|---|---|
| 1-(4-Aminophenyl)-7,8-(methylenedioxy)-3,5-dihydro-4H-2,3-benezodiazepin-4-one | Purdue Pharma | WO 9734878 |
| 6-(4-Pyridinyl)-1H-1,2,3-triazolo[4,5-a]pyrimidin-4(5H)-one | Sanofi-Synthelabo | Pharmaprojects No. 4466 |
| SH-608 | Schering | Pharmaprojects Accession No.: 26086 |
| ZK-200.755-2 | Schering | Pharmaprojects Accession No.: 33520 |
| ZK-200775 7-Morpholino-2,3-dioxo-6-trifluoromethyl-1,2,3,4-tetrahydro-quinoxaline-1-methylphosphonic acid | Schering | WO94/25469 |
| EGIS-8332 7-Acetyl-5-(4-aminophenyl)-8,9-dihydro-8-methyl-7H-1,3-Dioxolo[4,5-h][2,3]benzodiazepine-8-carbonitrile | Egis Pharmaceuticals Servier | WO 9907707 |
| EGIS-9637 [+/−]-1-[4-Aminophenyl]-3-[N-cyclopropyl-carbamoyl]-4-methyl-7,8-methylenedioxy-5H-3,4-dihydro-2,3-benzodiazepine | Servier | Pharmaprojects Accession No.: 29987 |
| EGIS 7444 7-Nitro-2,3-dioxo-N-[2-(1-piperidinyl) ethyl]-1,2,3,4-tetrahydroquinoxaline-6-sulfonamide | Egis Pharmaceuticals | ADIS R&D Insight Accession Number: 9703 |
| S-17625 6,7-Dichloro-2(1H)-oxoquinoline-3-phosphonic acid | Servier | British Journal of Pharmacology, (Apr. 1995) Vol. 114, Supp. S, pp. P330. |
| S-347301 7-Chloro-6-sulfamoyl-2-(1H)-quinoleinone-3-phosphonic acid | Servier | Drugs of the Future. 27 (Suppl. A): 203 (plus poster), Sep. 2002. France |
| S-1746 | Shionogi & Co., Ltd. | Pharmaprojects Accession No.: 32690 |
| SYM 2189 1-Methyl-6-methoxy-4-(4-aminophenyl)-2-(3-propylamino)carbonyl-1,2-dihydrophthalazine | Annovis | Society for Neuroscience Abstracts. 25: 1490, Part 2, Jan. 1, 1999. USA |
| SYM 2206 1-Methyl-6,7-dioxamethyl-4-(4-aminophenyl)-2-(3-propylamino)carbonyl-1,2-dihydrophthalazine | Annovis | 211th American Chemical Society National Meeting. 211: abstr. 110, Mar. 24, 1996. USA |
| SYM-2207 4-(Aminophenyl)-1-methyl-6,7-(methylenedioxy)-N-butyl-1,2-dihydrophthalazine-2-carboxamide | Annovis | Journal or Medicinal Chemistry, 39(2), 343–346, 1996 |
| SYM 2229 6,7-Dioxamethyl-4-(4-aminophenyl)-2-(3-propylamino)carbonyl-1,2-dihydrophthalazine | Annovis | Society for Neuroscience Abstracts. 26: 904, Part 1, 2000 |
| SYM 2259  | Annovis | ADIS R&D Insight Accession Number: 15391 |
| SYM-2267 | Transgenomic | 224th ACS National Meeting, Boston, MA, United States, Aug. 18–22, 2002 (2002), MEDI-255 Publisher: American Chemical Society, Washington, D.C. |
| YM90K 1,4-Dihydro-6-(1H-imidazol-1-yl)-7-nitro-2,3-Quinoxalinedione monohydrochloride | Yamanouchi Pharmaceutical Co., Ltd. | WO92/07847 |

-continued

| Compound name | Original supplier company | References, etc. |
|---|---|---|
| TQX 173<br>7-Chloro-4-oxo-8-(4H-1,2,4-triazol-4-yl)-<br>4,5-dihydro-[1,2,4] triazolo [1,5-a]<br>quinoxaline-2-carboxylic acid | University of Florence | Journal of Medicinal Chemistry.<br>43: 3824–3826, Oct. 19, 2000.<br>Italy. |
| Kaitocephalin<br>3-[5-[2-[[(3,5-Dichloro-4-hydroxy)<br>phenylcarbonyl] amino] carboxyethyl]-2-<br>carboxypyrrolidin-2yl]-Serine | Tokyo University | Society for Neuroscience<br>Abstracts. 24: 465, Part 1, 1998 |

RN:CAS Registry Number

The compounds described above can be produced with reference to the synthetic methods described in the references or using general synthetic methods. Otherwise, these compounds may be available from companies having produced, marketing, and having developed these compounds and the like.

The therapeutic agent of the present invention may further be used in combination with other pharmaceutical agents. For example, the antagonists against AMPA receptor may be administered singly or in combination with other antitumor drugs or other growth inhibitors or other pharmaceutical agents or nutritious agents.

Numerous antitumor drugs have been commercially available or under way of development so far. These can be selected as pharmaceutical agents to be concurrently used in combination for treating glioblastoma. Such antitumor drugs include for example antibiotic drugs, alkylating agents, metabolic antagonists, immunological agents and interferon-type agents. Specifically, the antitumor drugs are for example interferon-beta (immunoenhancer interferon), nimustine hydrochloride (alkylating agent), ranimustine (alkylating agent), etoposide (alkaloid), carboplastin and cisplatin (platinum formulation) and temozolomide (alkylating agent).

A pharmaceutical formulation containing the compound for use in accordance with the present invention or one type or two types or more of the salt thereof as the active ingredients are prepared, using carriers, excipients and other additives for general use in formulation.

The carriers and excipients for formulation may be solid or liquid, and include for example lactose, magnesium stearate, starch, talc, gelatin, agar, pectin, gum arabic, olive oil, sesame oil, cacao butter, and ethylene glycol and other routine such ones.

Administration thereof may satisfactorily be either oral administration via tablets, pills, capsules, granules, powders, liquids and the like or parenteral administration via injections via intravenous injections, intramuscular injections and the like, suppositories and transcutaneous agents.

The dose is appropriately determined, depending on each case, in terms of the symptom, age, sex and the like of a subject to be dosed. Generally, the daily dose of the compound of the present invention is about 100 to 2,000 mg per adult per day, preferably about 900 mg per adult per day. 100 to 2,000 mg per adult per day by dividing the daily dose into one or two to four doses per day. In case of intravenous administration or sustained intravenous administration, the administration may satisfactorily be administered for one hour to 24 hours per day.

As described above, the dose can be determined by taking into consideration various conditions. A dose less than the range described above may also be used in case that the dose is effective.

The compound for use in accordance with the present invention is mainly administered by parenteral administration, specifically including subcutaneous administration, intramuscular administration, intravenous administration, transcutaneous administration, intrahecal administration, epidural administration, intra joint administration and local administration, or may also be administered in various dosage forms, for example by oral administration if possible.

The injections for parenteral administration include for example sterile, aqueous or non-aqueous solutions, suspensions and emulsions. The aqueous solutions and suspensions include for example distilled water for injections and physiological saline. The non-aqueous solutions and suspensions include for example propylene glycol, polyethylene glycol, vegetable oils such as olive oil, alcohols such as ethanol, and Polysorbate 80 (under trade name). Such composition may contain auxiliary agents such as preservatives, moistening agents, emulsifying agents, dispersing agents, stabilizers (for example, lactose) and dissolution auxiliary agents (for example, meglumine). These are sterilized by filtering through bacteria-retaining filters, blending sterilizing agents, or irradiation. Alternatively, these may be produced once into a sterile solid composition and then dissolved or suspended in sterile water or sterile solvents for injections, prior to use.

As the solid composition for oral administration, tablets, powders, granules and the like are used. In such solid composition, one or more active substances are mixed with at least one inert excipient, for example lactose, mannitol, glucose, hydroxypropyl cellulose, microcrystalline cellulose, starch, polyvinyl pyrrolidone, metasilicic acid and magnesium aluminate. According to general methods, the composition may contain inert additives other than diluents, lubricants for example magnesium stearate, disintegrators for example fibrin calcium glucorate, stabilizers such as lactose and dissolution auxiliary agents such as glutamate or aspartic acid. On a needed basis, the tablets or pills may satisfactorily be coated with sugar coating or with films of stomach-soluble or gut-soluble substances such as sucrose, gelatin, hydroxypropyl cellulose and hydroxypropylmethyl cellulose phthalate.

The liquid composition for oral administration includes for example pharmaceutically acceptable emulsions, liquids, suspensions, syrups and elixirs and contains inert diluents for general use, for example distilled water and ethanol. The composition may contain auxiliary agents such as moistening agents and suspending agents, sweetening agents, flavoring agents, aromatic agents and preservatives, other than the inert diluents.

EXAMPLES

The present invention is now described in detail in the following Examples. However, the invention should not be limited to those in the following Examples.

The therapeutic effect of the present invention was confirmed by the following experimental method.

Experimental Example 1

Growth Inhibition of Glioblastoma In Vitro

Human glioblastoma cell (CGNH-89 cell line) was used at this experiment. These cells were randomly divided in the following three groups: a group of a glutamate-free medium (no glutamate group; control group); a group of the glutamate-free medium added 100 μM glutamate (100 μM glutamate group); a group of the glutamate-free medium added 100 μM glutamate and 20 μM NBQX (100 μM glutamate+20 μM NBQX group). The cells were incubated for 48 hours. The CGNH-89 cell was cultured in DMEM (Dulbecco's modified Eagle's medium) supplemented with 10% dialyzed fetal calf serum.

CGNH-89 Cell Line

CGNH-89 cell line was established through resection from the tumor at the right front lobe of a 56-year old lady according to the Explant method by Nicolas et al. (Science 196, 60-63, 1977). The cell line shows activities of glia cell fibrous acidic protein (GFAP), vimentin, A2B5, 04 and myelin basic protein (J. Neuropathol. Exp. Neurol., 57653-663, 1998). Additionally, the mRNAs of GluR1 through GluR4 were analyzed with antibodies against the AMPA receptor subunits GluR1, GluR2, GluR3 and GluR4 and RT-PCR. Consequently, the cell line expresses GluR1 and GluR4 but not expresses GluR2 and GluR3. As described above, the cell line has the same profile as that of the cell of primary glioblastoma de novo.

Furthermore, the cell line is provided by the inventor and is available on request to? the inventor.

The anti-tumor action was evaluated by calculating the apoptosis score by TUNEL method (terminal deoxynucleotide transferase (TdT)-mediated dUTP nick end labeling) 48 hours after culturing. Additionally, proliferation of the human glioblastoma cell was evaluated, using the antibody Ki67.

The results are shown as mean±standard deviation and statistically analyzed by the Student's t-test. Significance level was set at p<0.05.

Test Results

In the no glutamate group, apoptosis was induced in 18% of the human glioblastoma cells within the 48-hour incubation period. Additionally, almost no proliferation was observed. In contrast, the addition of 100 μM glutamate to the culture medium decreased the apoptosis down to 3%, while the proliferative activity increased to 18.5%. Meanwhile, NBQX as an antagonist against AMPA receptor inhibited the action of suppressing apoptosis as induced by glutamate, so that NBQX induced the apoptosis. Additionally, NBQX suppressed the glutamate-induced proliferative activity (Table 1).

TABLE 1

Anti-tumor action of antagonist NBQX against AMPA receptor

| Dosed group | TUNEL-SCORE (ratio of apoptosis) | staining index with Ki-67 (proliferation inhibiting activity) |
|---|---|---|
| No glutamate group (control) | 18.0 ± 2.5% | <0.1% |
| 100 μM glutamate group | 3.0 ± 2.0% | 18.5 ± 3.0% |
| 20 μM NBQX + 100 μM glutamate group | 13.0 ± 2.0%* | 2.0 ± 1.0%** |

TUNEL-SCORE: The number of TUNEL positive cell meaning a cell with DNA fragmented by apoptosis in the microscopic field of vision divided by the number of total cells represented as PI (propidium iodine) positive nucleus in the same field of vision is shown as TUNEL SCORE.
Staining index with Ki-67: The number of Ki-67 positive cells in the microscopic field of vision as divided by the number of total cells represented as PI (propidium iodine) positive nucleus in the same field of vision is shown as the staining index.
*p < 0.03
**p < 0.001.

Based on the results, it was confirmed that the AMPA receptor antagonist inhibits the suppression of the apoptosis by glutamate and inhibits glutamate-induced proliferation of glioblastoma in vitro.

Experimental Example 2

Growth Inhibition on the Glioblastoma (Human Glioblastoma) In Vivo

Nude mice (5-6 weeks old) were used at this experiment. $10^7$ cells of CGNH-89 used in Example 1 were transplanted subcutaneously in the nude mice. On the next day of transplantation, the mice were divided randomly in two groups; a group (n=12) to be administered with 100 mg/kg compound A and a group (n=12) to be administered with PBS (phosphate buffered saline). The drug was administered repeatedly intraperitoneally for 14 days starting on the next day of transplantation. Up to day 8 after the completion of the administration, the mice were observed. The tumor size was measured every two days with a vernier micrometer, to calculate the volume according to the formula (length×width$^2$)×½.

The results are shown in mean±standard deviation and statistically analyzed by the Student's t-test. The significance level was set at p<0.05.

Test Results

Figure 1:
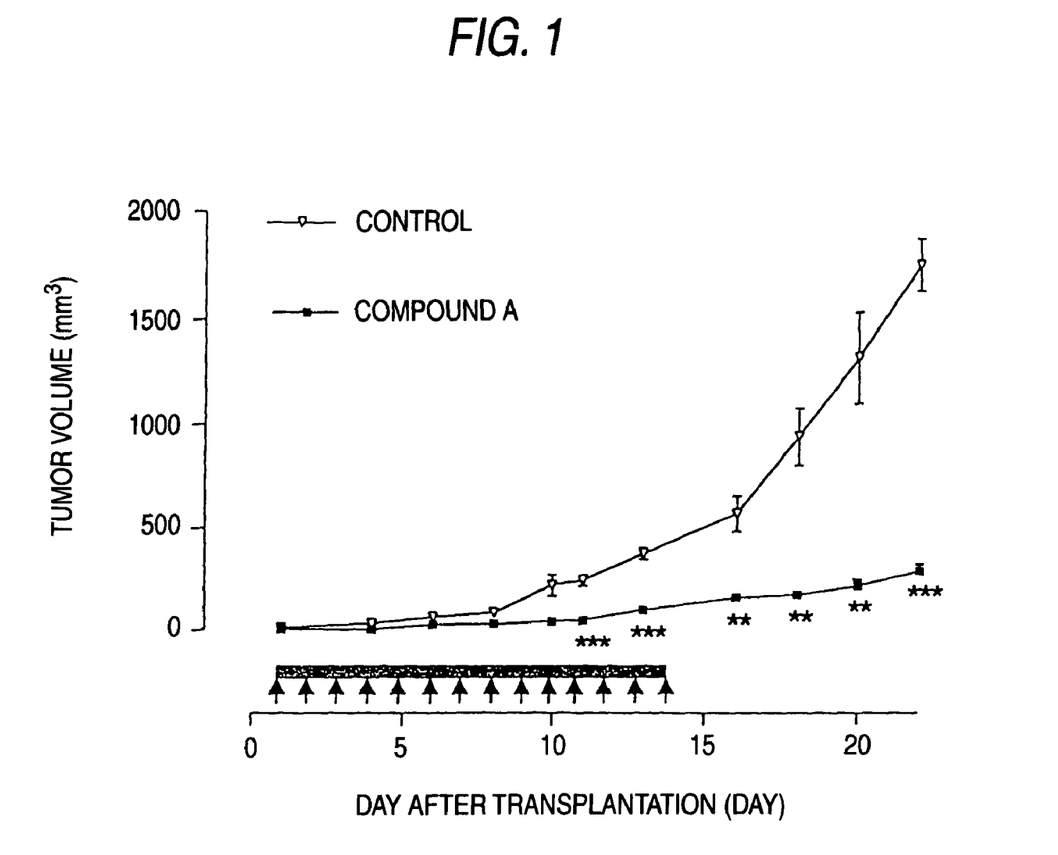
FIG. 1 shows a graph of tumor volumes in animals administered intraperitoneally with control (PBS) and 100 mg/kg compound A in a repeated manner for 14 days from the next day of tumor transplantation.

Compound A as an antagonist against AMPA receptor expressed a significant tumor growth inhibition on days 11 and 13 after the onset of administration and on days 2, 4, 6 and 8 after the completion of administration (FIG. 1).

Based on the results, it was confirmed that the antagonist against AMPA receptor showed an excellent tumor growth inhibition even in vivo on the glioblastoma cell with the pathological feature of human glioblastoma.

Experimental Example 3

Growth Inhibition on Glioblastoma (Human Glioblastoma) in the Orthotopic Xenograft Model Using an orthotopic xenograft model, in which CGNH-89 is transplanted in the brain parenchyma of mouse or rat, the anti-tumor effect of an antagonist against AMPA receptor is evaluated. The dose of compound A is 50 mg/kg or 10 mg/kg. On the next day of the transplantation of the tumor, intraperitoneal administration of compound A started for 14 days. On day 21, a specimen is prepared for pathological analysis.

Example

Production of Freeze-Dried Formulation 33.3 g of meglumine was dissolved in 400 ml of distilled water for injections, to which 10 g of compound A was added for dissolution with stirring. 1,400 ml of distilled water for injections was added to the resulting solution. Additionally, 40 g of mannitol was dissolved in the solution, to which distilled water for injections was added to 2,000 ml. The resulting solution was filtered aseptically by general method. 15 ml of the resulting filtrate was charged in a 30-ml vial and freeze-dried by general method, to prepare a freeze-dried formulation of the compound for use in accordance with the present invention.

INDUSTRIAL APPLICABILITY

In accordance with the present invention, compounds with an antagonistic action against AMPA receptor, which is preferably zonanpanel or a salt or hydrate thereof or NBQX, are useful as therapeutic agents of glioblastoma, particularly primary glioblastoma de novo with a high malignancy level.

The invention claimed is:

1. A method for treating glioblastoma comprising administering a therapeutically effective amount of a compound having an activity of inhibiting an α-amino-3-hydroxy-5-methyl-4-isoxazole propionic acid (AMPA) receptor to a patient with the disease, wherein the compound is [7-(1H-imidazol-1-yl)-6-nitro-2,3-dioxo-3,4-dihydroquinoxalin-1(2H)-yl]acetic acid or a salt thereof; 2,3-dihydroxy-6-nitro-7-sulfamoyl-benzo(F)-quinoxaline or a salt thereof; 2-[N-(4-chlorophenyl)-N-methylamino]-4H-pyrido[3,2-e]-1,3-thiazin-4-one or a salt thereof; 1-(4-aminophenyl)-4-methyl-7,8-methylenedioxy-5H-2,3-benzodiazepine or a salt thereof, or 7-acetyl-5-(4-aminophenyl)-8(R)-methyl-8,9-dihydro-7H-1,3-dioxolo[4,5-h][2,3]benzodiazepine or a salt thereof.

2. A method according to claim 1, wherein the compound having an activity of inhibiting an AMPA receptor is 7-acetyl-5-(4-aminophenyl)-8(R)-methyl-8,9-dihydro-7H-1,3-dioxolo[4,5-h][2,3]benzodiazepine or a salt thereof.

* * * * *